United States Patent [19]
Esler et al.

[11] Patent Number: 5,838,008
[45] Date of Patent: Nov. 17, 1998

[54] METHOD AND APPARATUS FOR MEASURING GAS CONCENTRATIONS AND ISOTOPE RATIOS IN GASES

[75] Inventors: Michael Brian Esler, Wollongong; David William Tracy Griffith, Mangerton, both of Australia

[73] Assignee: University of Wollongong, Wollongong, Australia

[21] Appl. No.: 770,739

[22] Filed: Dec. 18, 1996

[51] Int. Cl.[6] .................................................. G01J 5/02
[52] U.S. Cl. ............................. 250/339.08; 350/393.07; 350/341.5
[58] Field of Search ....................... 250/339.07, 339.08, 250/341.5, 343

[56] References Cited

U.S. PATENT DOCUMENTS

| | | | |
|---|---|---|---|
| 5,303,165 | 4/1994 | Ganz et al. | 364/571.9 |
| 5,341,206 | 8/1994 | Pittaro et al. | 356/301 |
| 5,416,325 | 5/1995 | Buontempo et al. | 250/339.08 |
| 5,448,070 | 9/1995 | Day et al. | 250/339.07 |
| 5,578,499 | 11/1996 | Ismail | 436/524 |

FOREIGN PATENT DOCUMENTS

| | | |
|---|---|---|
| A75073/91 | 10/1991 | Australia . |
| A24903/95 | 1/1996 | Australia . |

OTHER PUBLICATIONS

PCT International Search Report, dated Feb. 27, 1998, (4pp.).

I. L. Marr, A. Kindness and M. S. Cresser, "Measurement of [14]N: [15]N Ratios by Fourier Transform Infrared Spectrometry," *The Analyst*, Nov. 1987, vol. 112, pp. 1491–1494.

A. Kindness and I. L. Marr, "Measurement of Carbon–13: Carbon–12 Ratios by Fourier Transform Infrared Spectrometry," *The Analyst*, Feb. 1996. vol. 121, pp. 205–209.

M. B. Esler, D. W. T. Griffith, S. R. Wilson and L. P. Steele, "Precise Measurement of Trace Gas Mixing Ratios and $^{13}$C/[12]C Isotope Ratio in air Using FTIR Spectroscopy." No date.

M. B. Esler, D. W. T. Griffith, S. R. Wilson and L. P. Steele, "Carbon Monoxide, Nitrous Oxide, Methane and Carbon Dioxide Trace Gas Analysis by Fourier Transform Infrared (FTIR) Spectroscopy," *Program Reports—Trace gases*, pp. 117–118. No date.

L. Tyson, T. J. Vickers and C. K. Mann, "Infrared Spectrophotometric Determination of [12]C Enrichment," *Applied Spectroscopy*, vol. 38, No. 5, 1984, pp. 697–700.

(List continued on next page.)

*Primary Examiner*—David P. Porta
*Assistant Examiner*—David Vernon Bruce
*Attorney, Agent, or Firm*—Ratner & Prestia

[57] ABSTRACT

A method of determining a trace gas concentration in a gas sample utilizing Fourier Transform Infrared Spectroscopy. The method includes the steps of (i) synthetically calibrating a spectrometer, and
(ii) determining a spectral window within which to fit a calculated spectral trace to an experimental spectral trace by
   (a) choosing a series of candidate windows;
   (b) determining the likely error measure associated with a fitting of the spectral trace for each of the series of candidate windows;
   (c) utilizing the likely error measure associated with each of the fitting to determine a final window having substantially the lowest likely error measure; and
   (d) utilizing the final window as the spectral window.

The calibration and the spectral window is then utilized to fit a calculated spectral trace to a spectral trace measured by the spectrometer and to determine the concentrations of constituent gases.

23 Claims, 8 Drawing Sheets

OTHER PUBLICATIONS

D. W. T. Griffith, "Synthettic Calibration and Quantitative Analysis of Gas Phase FTIR Spectra," pp. 79–80. No date.

D. W. T. Griffith, "Synthetic Calibration of Quantitative Analysis of Gas–Phase FT–IR Spectra," *Applied Spectroscopy*, vol. 50, No. 1, 1996, pp. 59–70.

B. Galle, L. Klemedtsson and D. W. T. Griffith, "Application of a Fourier transform IR system for measurements of $N_2O$ fluxes using micrometerological methods, an ultralarge chamber system, and conventional field chambers," *Journal of Geophysical Research*, vol. 99, No. D8, Aug. 20, 1994, pp. 16,575–16,583.

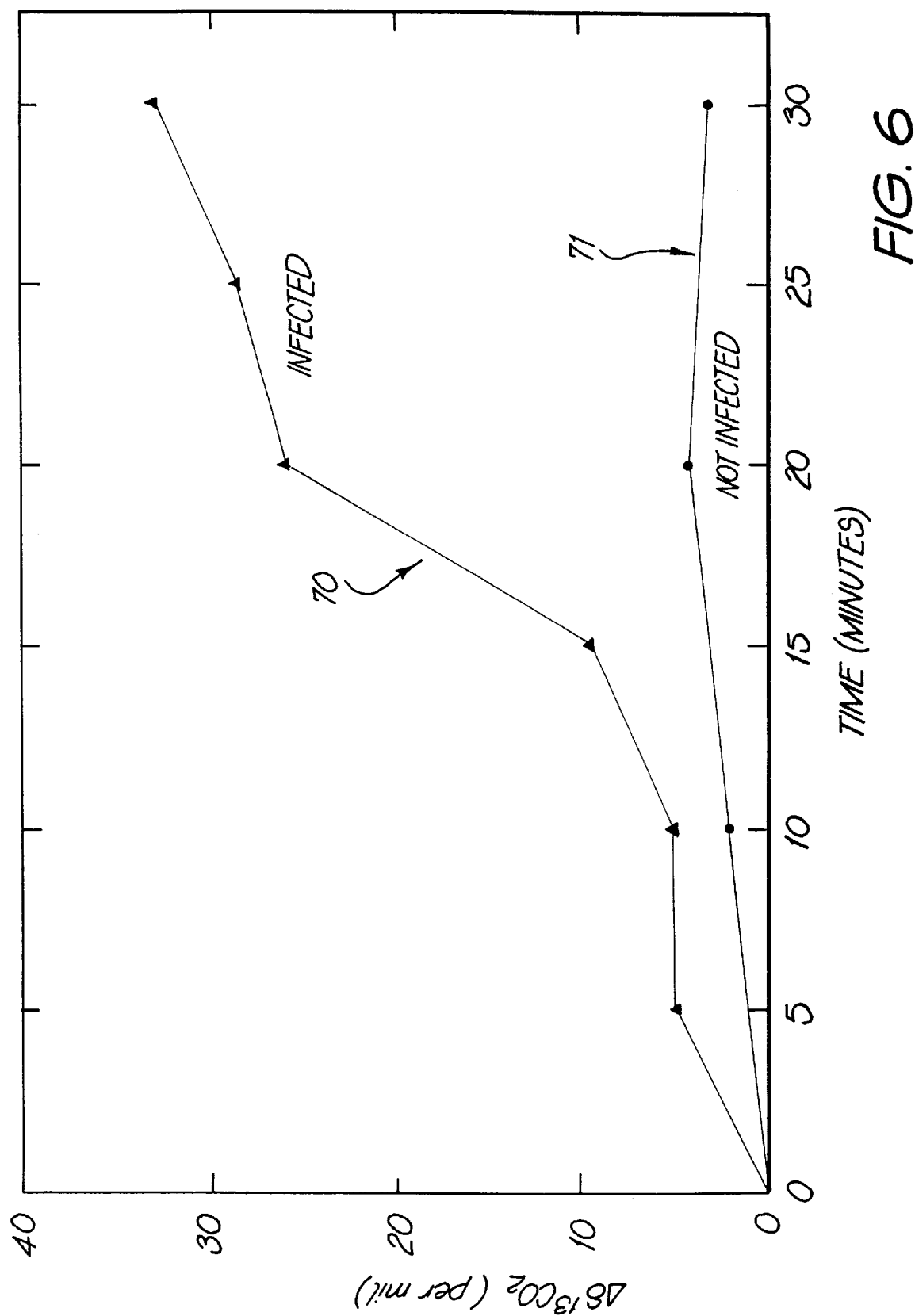

METHOD AND APPARATUS FOR MEASURING GAS CONCENTRATIONS AND ISOTOPE RATIOS IN GASES

FIELD OF THE INVENTION

The present invention relates to the utilisation of spectrographic techniques such as Fourier Transform Infrared Spectroscopy (FTIR) to measure gas concentrations and ratios of concentrations and has particular application to the measurement of isotope ratios.

BACKGROUND OF THE INVENTION

It is often necessary to precisely and accurately measure the concentrations of trace gases in air and other gas-phase samples (for example, breath, combustion products, landfill gas, etc.). "Trace" gases are typically those that exist in only a very small quantity in a given sample.

For example, in "clean air" the mixing ratios of several trace gases are approximately:

| | |
|---|---|
| carbon dioxide ($CO_2$) | 360 ppmv (parts per million by volume; million = $10^6$) |
| methane ($CH_4$) | 1.7 ppmv |
| nitrous oxide ($N_2O$) | 310 ppbv (parts per billion by volume; billion = $10^9$) |
| carbon monoxide (CO) | 50 ppbv. |

These low mixing ratios are difficult to measure accurately. Currently the most common successful techniques are based on gas chromatography and Non-Dispersive Infrared spectroscopy (NDIR). Isotope ratios are most commonly measured by Isotope Ratio Mass Spectrometry.

Unfortunately, gas chromatography and NDIR processes can normally only be configured to measure one or two trace gases at a time. Further Isotope Ratio Mass Spectometers can measure isotope ratios but cannot usually measure isotopomer concentrations.

Further, the cost of equipment using these techniques can often be prohibitive and can be unduly complex to operate. Further, unfortunately, FTIR units presently available have not been sufficiently sensitive to measure these trace gases precisely and accurately at such low concentration levels.

The use of FTIR techniques often utilises a multi-pass cell such as a White cell to measure test samples. This increases the pathlength and hence the sensitivity of the method.

Referring now to FIG. 1(a) to 1(f) there is illustrated in FIG. 1(a) an example intensity spectrum which is obtained when a White cell is evacuated. The intensity spectrum 1 gives a measure of the intensity of the infrared light leaving the infra-red light source, travelling through White cell where no sample is encountered and in striking the infrared detector.

In FIG. 1(b), there is illustrated the spectrum acquired after filling the White cell with a "clean air" sample. This gives a measure of the intensity of the infrared light reaching the detector after encountering the absorbing molecules in the sample. In comparison with the spectrum of FIG. 1(a), the spectrum of FIG. 1(b) exhibits a strong absorption feature 2 near the 2400 $cm^{-1}$ wave number due to carbon dioxide absorption.

In FIG. 1(c) there is illustrated the "absorbance" spectrum 3 which is obtained by taking the log of the ratio of the spectrum of FIG. 1(a) and FIG. 1(b). The resulting spectrum 3 is primarily of the air sample, as the contributions due to the infrared source spectrometer, White cell and infrared detector will generally cancel out in the ratio. Hence, the absorption features may be directly proportional to the concentration of the trace gas species. The two significant peaks 5, 6 are due to $CO_2$ absorption and $CH_4$ absorption respectively.

In FIG. 1(d), there is shown the expansion of the boxed region 7 of FIG. 1(c), revealing greater detail with the spectral lines due to $^{12}CO_2$ 9 and $^{13}CO_2$ 10 clearly illustrated. In "clean air" the concentration of $^{12}CO_2$ is approximately 90 times that of $^{13}CO_2$. The fine structure in the spectrum is due to contributions from individual rotational quantum states.

An expansion of the boxed region 12 of FIG. 1(d) is illustrated in FIG. 1(e). The fine structure 10 of the $^{13}CO_2$ spectrum is shown in more detail as well as the very weak absorption features of $N_2O$ 14 and CO 15. Further expansion of the region 16 shows further details of the $N_2O$ 14 and CO 15 absorption features. The species are present in air at less than one thousandth the abundance of $CO_2$.

Unfortunately, current FTIR instrumentation has to date been unsuccessful in resolving such detailed features with sufficient quantitative precision and accuracy for many applications such as clean air monitoring.

SUMMARY OF THE INVENTION

It is an object of the present invention to provide a method and apparatus for the more accurate and precise measurement of concentrations of trace gases such as those illustrated by FIGS. 1(c) to 1(f).

In accordance with a first aspect of the present invention there is provided a method of performing a primary calibration of a spectrometer device comprising the steps of:

calculating a theoretical spectral response function for a series of candidate chemical substances;

convolving said theoretical spectral response function with a spectrometer instrument response function corresponding to said spectrometer device so as to produce an expected response function for the series of candidate chemical substances; and utilising said expected response function as the calibration of the spectrometer device in the subsequent measurement of chemical substances.

Preferably, the method further comprises the step of measuring a series of calibrated standard chemical substances to determine a subsequent calibration of said spectrometer device and said utilising step further comprises utilising said subsequent calibration and the primary calibration as the calibration of the spectrometer device.

Preferably the theoretical response function includes correction factors associated with at least one of Doppler broadening, pressure broadening or temperature correction of the spectral response.

Preferably, the spectrometer instrument response function includes correction factors associated with at least one of field of view, spectral resolution, apodization, spectral noise or wave number shift.

In accordance with a further aspect there is provided a spectral window within which to fit a synthetically calculated spectral trace to an experimentally determined spectral trace.

In accordance with a further aspect of the present invention there is provided a method of determining a spectral window within which to fit a synthetically calculated spectral trace to an experimentally determined spectral trace, the method comprising the steps of:

choosing a series of candidate windows;

determining a likely error measure associated with the fitting of said spectral trace for each of the series of candidate windows;

utlising the likely error measure associated with each of fitted regions to determine a final window having substantially the lowest likely error measure; and utilising the final window as said spectral window.

Preferably the fitting procedure comprises a least squares fit of the measured spectrum by a synthetic spectrum.

In accordance with a further aspect of the present invention there is provided a method of determining a trace gas concentration in a gas sample utilising Fourier Transform Infra-Red Spectroscopy, the method comprising the following steps (i) to (iii) of:

(i) synthetically calibrating a spectrometer by the steps of:
  (a) calculating a theoretical spectral response function for a series of candidate chemical substances;
  (b) convolving the theoretical spectral response function with a spectrometer instrument response function corresponding to the spectrometer device so as to produce an expected response function for the series of candidate chemical substances; and
  (c) utilising the expected response function as the calibration of the spectrometer device in the subsequent measurement of chemical substances;

(ii) determining a spectral window within which to fit a calculated spectral trace to an experimental spectral trace by the steps of:
  (a) choosing a series of candidate windows;
  (b) determining the likely error measure associated with a fitting of the spectral trace for each of the series of candidate window;
  (c) utlising the likely error measure associated with each of the fitted regions to determine a final window having substantially the lowest likely error measure; and
  (d) utilising the final window as the spectral window; and (iii) utilising the calibration and the spectral window to fit a calculated spectral trace to a spectral trace measured by the spectrometer and to thereby determine the concentration of constituent gases.

The present invention is particularly advantageous in measuring the ratio of a $^{12}C$ to $^{13}C$ isotopes, especially when composed in carbon dioxide form.

The present invention has particular utility in the measurement by Fourier Transform Infrared Spectroscopy (FTIR) techniques of trace gases that are contained in a patient's breath samples.

The present invention further has particular advantages in allowing multiple trace gases to be simultaneously measured through FTIR techniques.

BRIEF DESCRIPTION OF THE DRAWINGS

Notwithstanding any other forms which may fall within the scope of the present invention, preferred forms of the invention will now be described, by way of example only, with reference to the accompanying drawings in which:

FIG. 6 illustrates plots of $^{13}CO_2$, $^{12}CO_2$ isotope ratios in the breath of *Helicobacter pylori* infected and non-infected patients.

DESCRIPTION OF PREFERRED AND OTHER EMBODIMENTS

Figure 1A:
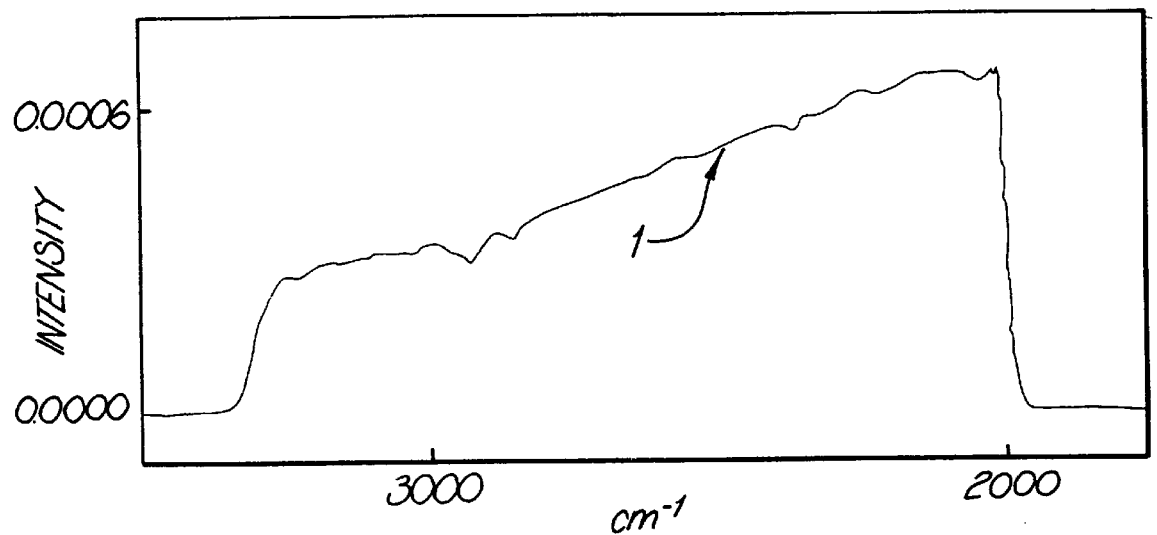
FIG. 1(a) to FIG. 1(f) illustrate example spectral plots of a clean air sample.
Figure 1B:
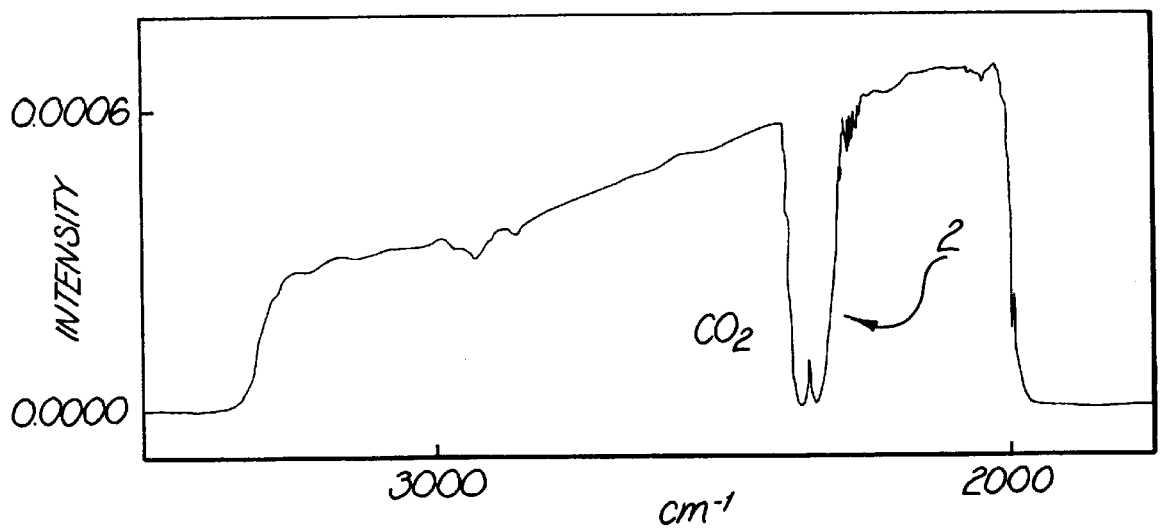
Figure 1C:
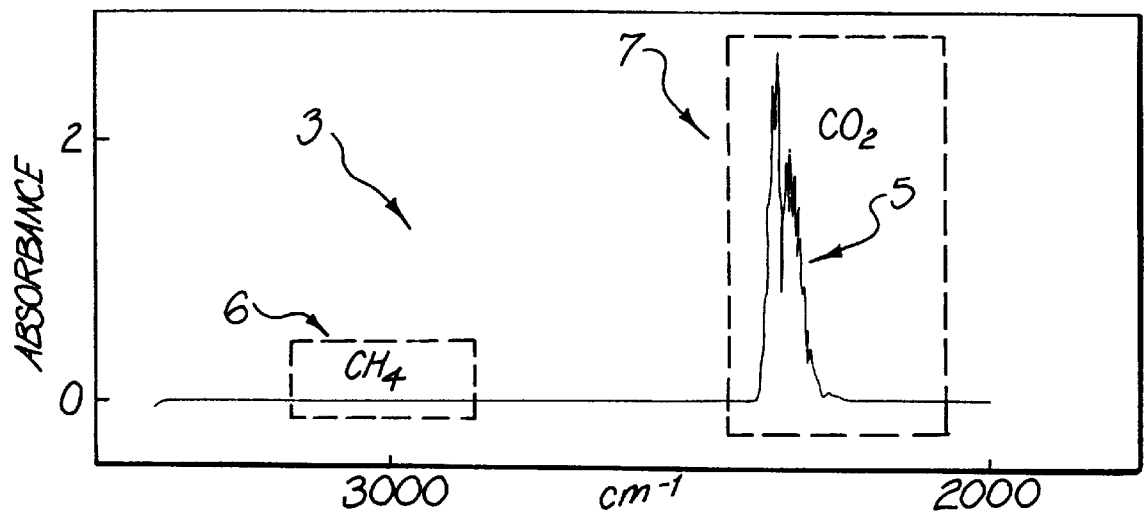
Figure 1D:
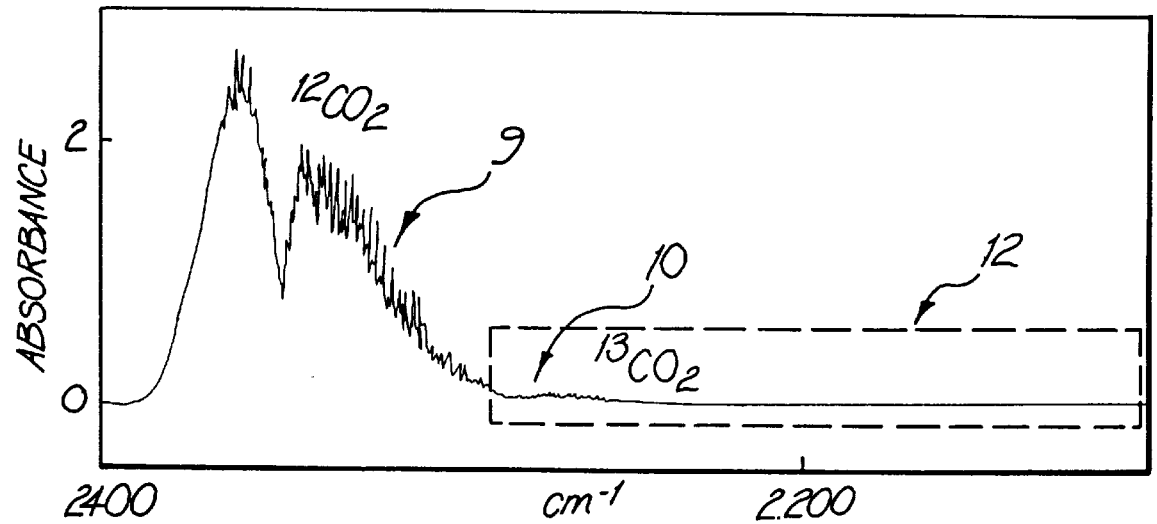
Figure 1E:
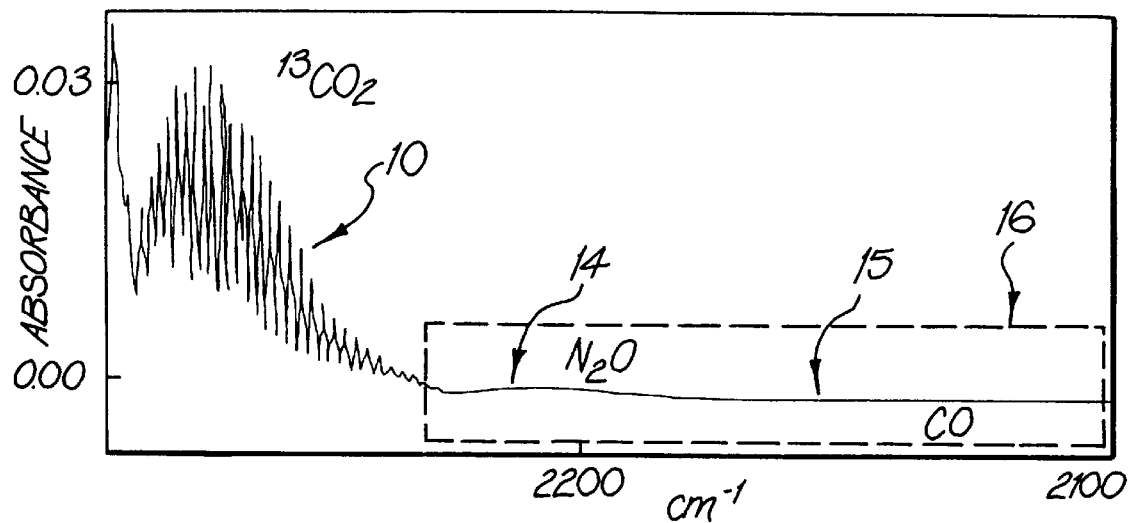
Figure 1F:
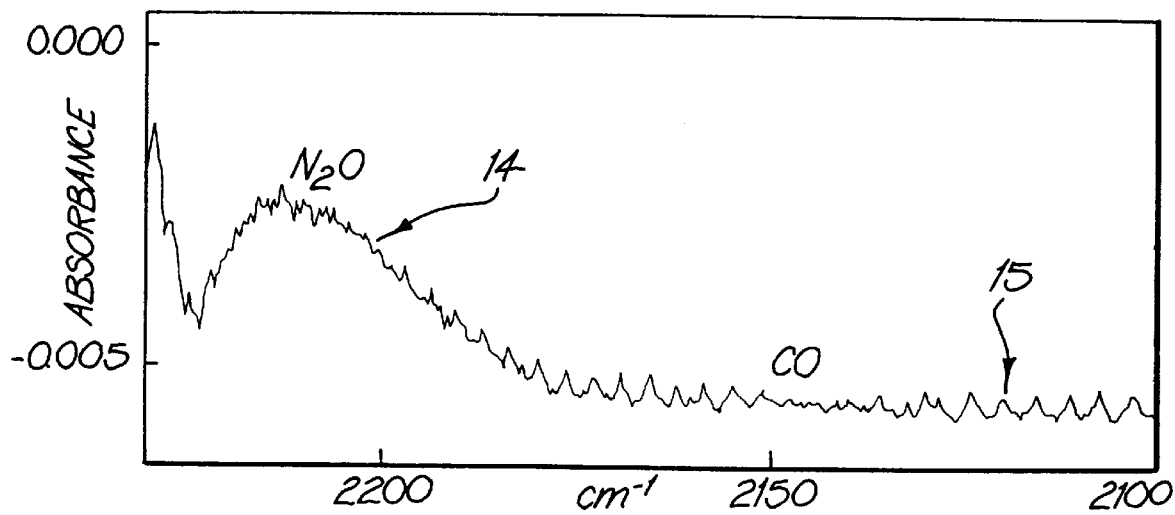
Figure 2:
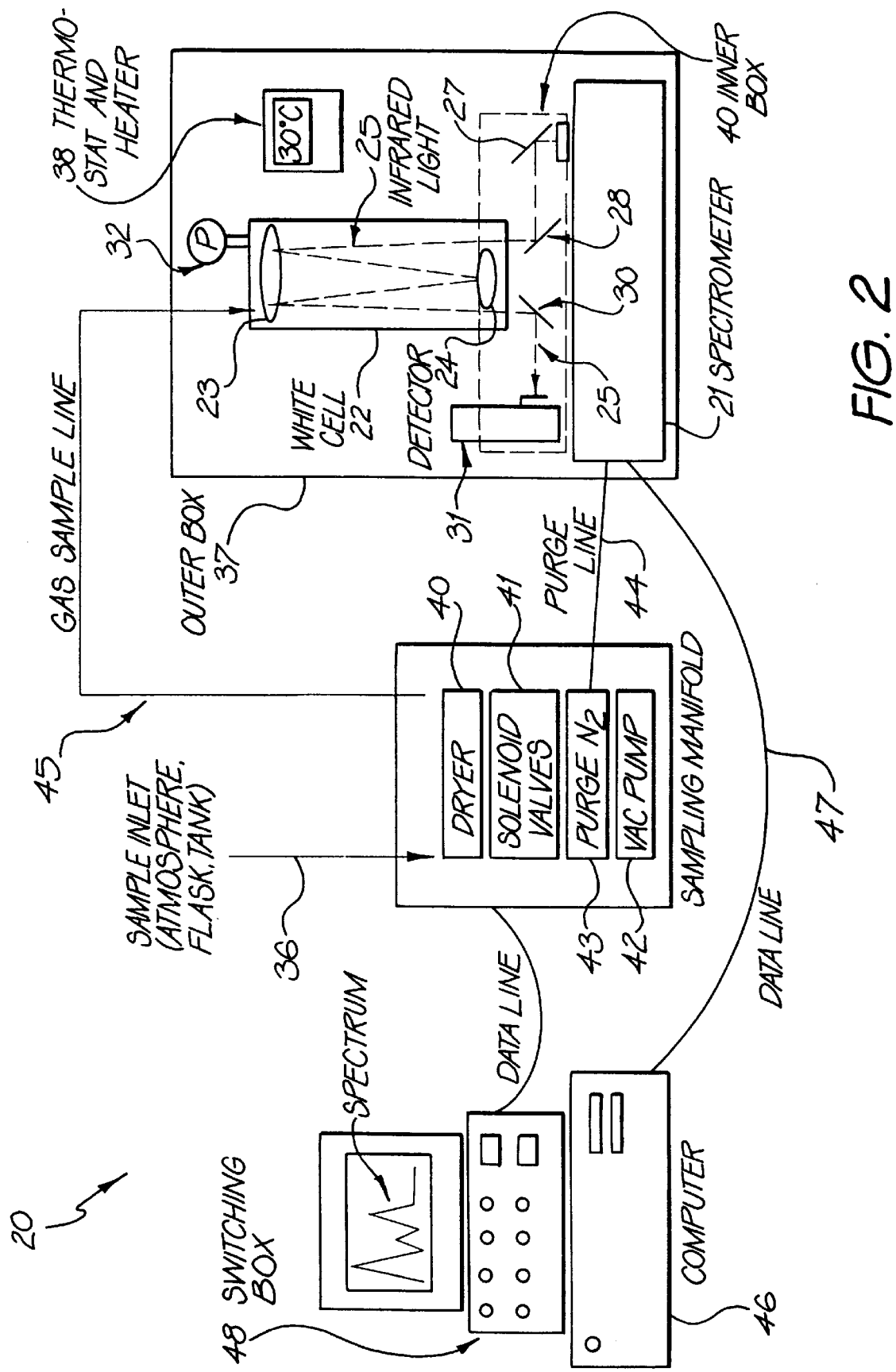
FIG. 2 illustrates, in schematic form, the preferred embodiments.

Referring now to FIG. 2, there is schematically illustrated the preferred embodiment 20 for conducting trace measurements. The arrangement 20 includes a Bomen MB100 FTIR spectrometer 21 having a maximum resolution of 1 $cm^{-1}$. The spectrometer is available from Bomen Inc. of Quebec, Canada. The spectrometer interacts with a White cell 22. The White cell utilised was obtained from Infrared Analysis Inc. of Anaheim, Calif., USA. The White cell 22 includes a multi-path gas cell having spherical mirrors 23, 24 at either end which causes an infrared beam 25 to traverse the length of the cell up to 40 times, thereby increasing the absorption of light due to interaction with the sample. The infrared beam 25 is projected from the spectrometer 21 by means of reflective mirrors 27, 28. Preferably, the use of the spherical mirrors 23, 24 results in a total path length of between 9.8 meters and 22.1 meters. After traversal of the White cell 22, the infrared light output is preferably reflected by mirror 30 before entering detector 31 which can comprise an Indium Antimonide (InSb) infrared light detector which is liquid nitrogen cooled. A MKS Baratron capacitance manometer 32 is utilised to measure the pressure conditions within the White cell 22.

In the preferred arrangement 20, it is very important to keep control of the environmental conditions of the White cell and spectrometer 22. In this respect, the White cell 22 detector 31 and spectrometer 21 were initially enclosed in an outer box 37 which was a purpose built unit and comprised a perspex box which was sealed so as to prohibit room air entering inside the outer box 37. It also acted as a thermal barrier between the room and the internal portions of box 37 thereby allowing the instrument to be accurately thermally controlled.

Mounted on the inside of the outer box 37 was a Eurotherm temperature controller, connected to a fan heater. This enabled the temperature of the internals of the outer box 37 to be stabilised to within a tenth of a degree Celsius, good temperature control being essential for the most precise measurements. Platinum RTD sensors were utilised to measure temperature at several points within the box 37. A further inner box 40 was constructed from perspex and fashioned to enclose the volume where the infrared beam 25 exited from the spectrometer 21 entered the White cell 22 and then entered the detector 31. The perspex box 40 was sealed so as to prohibit room air entering the box 40 and thereby affecting the infrared light beam 25. The perspex inner box 40 also maximised the efficiency with which the critical volume between the White cell 22, the spectrometer and the detector could be purged with nitrogen gas.

The sampling manifold 35 is constructed of copper, stainless steel and teflon tubing, and includes drier 40, solenoid valves 41, vacuum tank 42 and nitrogen purge pump 43. The sampling manifold as constructed in the conventional manner and allowed for the introduction into the White cell of samples 36 from the ambient atmosphere, a pressurised gas cylinder, a small glass sample flask or sample bag as required. The vacuum pump 42 was connected to the manifold for use in removing the sample from the White cell after analysis. The spectrometer 21 and inner box 40 were constantly purged via purge line 44 with clean, dry nitrogen gas to ensure that the only absorbing molecules that the infrared beam encountered are those intentionally introduced into the White cell via gas sample line 45.

An analysis and control computer 46 was utilised which comprised an IBM PC-compatible type machine utilising a 486 Intel Processor. The supplied Bomen interface card was utilized to allow for communication 47 between the computer 46 and spectrometer 21 for data acquisition of the spectrum. Also, the computer 46 had installed a conventional Strawberry Tree mini-16 data acquisition and control card (available from Strawberry Tree, Calif., USA). The data acquisition and control card allowed the automatic acquisition of pressure and temperature data through its analogue input channels and also allowed the opening and closing of the solenoid valves in the sampling manifold through its digital output channels.

A switching box 48 was also constructed to allow for the manual operation of the solenoid valves etc by moans of switches, the construction again being conventional.

It should be noted that, in the construction of the arrangement 20, it was found that some natural and man-made materials perturbed the trace gas mixing ratios obtained. For example, nylon tubing was found to be a significant source of carbon monoxide gas. Other polymers and elastomers were observed to perturb carbon dioxide concentrations, etc. Further, hydrocarbons, if not prevented from back diffusing from the rotary oil vacuum pump, were found to interfere with the spectroscopic measurements of methane which is also a hydrocarbon.

Drying of the samples to remove water from the resulting spectrum is also important. Many of the intense absorbance features due to $H_2O$ can interfere with the spectroscopic features of $CO$, $N_2O$ and $CH_4$ in particular. Some drying agents used for drying air, e.g. molecular sieves, are known to perturb trace gas concentrations and to alter the isotopic ratio of carbon dioxide passing through them. Therefore, drying is preferably carried out using drying agents in the sampling manifold which minimise or exclude the possibility of altering the sample measurements. Further, as noted previously, generally speaking, copper, teflon tubing, glass, un-lubricated brass, stainless steel and viton plumbing fittings were found to be suitable and magnesium perchlorate and/or Nafion™ drying systems available from Perma Pure Inc., New Jersey, USA, were found to be suitable.

It should be further noted that very small quantities are being measured utilizing the arrangement 20, and also very small changes in the quantities measured. It was found to be perilously easy to introduce perturbations into the system which will result in loss of measurement precision or incorrect results. Therefore, the care with which measurements must be taken is preferably of the highest order.

Each fully calibrated measurement of a sample was derived from the acquisition of up to four separate spectra. These are:

(1) the evacuated cell spectrum;

(2) the unknown sample spectrum which is ratioed to the former and the log taken to give the absorbance spectrum;

(3) the evacuated cell spectrum; and (4) a calibration sample spectrum (described below) which, when ratioed and the log taken, gives the absorbance spectrum of the calibration gas standard.

These four discrete experimental measurement events cannot occur simultaneously. The behaviour of the instrument may be subtly changing in time, thus introducing a source of error into the analyses of the spectroscopic data. This is not just a theoretical consideration but a very real effect. Much effort must be undertaken with the arrangement 20 to maximise the sensitivity and precision of the instruments utilised and identify and remove the sources of instability in the instruments utilised over time.

While there are certain gains to be made by reducing the signal to noise ratio of the spectra by scanning the sample for long periods, there is a point beyond which this is counter-productive if samples are measured too far apart in time. It was found that scanning for between 2 and 8 minutes was optimal, depending on the precise configuration of the instrument and the aim of the measurement and the sample being measured. Slight changes in temperature, sample pressure, sample or purge gas humidity, as well as slight changes in infrared source intensity and detector sensitivity in time can cause small changes in each measured single beam spectrum. The small changes in turn cause changes in the resulting absorbance spectra, which in turn perturbed the results obtained in calculation of concentrations. The best practice was found to be to make associated measurements as close to one another in time as possible, for example, the acquisition of an empty cell spectrum immediately followed by the acquisition of the actual sample spectrum. Frequent calibration with a standard gas when required is also preferable to infrequent calibration. Making all measurements at as close as possible to the same sample temperature and pressure was also found to be very important, hence the need for a thermostatic enclosure and for precise pressure measurement. All of these considerations attempt to remove from the spectra sources of variation apart from those it is aimed to measure, being the changes in the concentrations of the trace gases in the samples.

The spectrometer 21 and the inner box volume 40 were purged with high-purity nitrogen gas flowing at approximately 200 ml per minute. This ensured that the environment through which the infrared beam passes before entering the White cell and after leaving the White cell remains optically constant and contains as few absorbing molecules as possible. In addition, the nitrogen was further dried and scrubbed of CO, using Sofnocat catalyst (available from Molecular Products Ltd., Essex, United Kingdom) before entering the instrument purge line 44. The usual commercially supplied high purity nitrogen was found to contain relatively high and variable levels of CO, which could potentially compromise the precision of any CO analysis.

In principle, it is possible to analyse samples at a range of different pressure and temperature conditions and then correct the results to a single standard temperature and pressure by use of the Ideal Gas Law. This enables direct comparison of results obtained under varying conditions. In practice, however, the Ideal Gas Law is satisfactory only as a first order approximation. Second order effects may be large enough to compromise measurement precision. For example, the first order effect of increasing sample temperature from 300 K to 303 K at constant pressure will be a 1% decrease in the density of the gas sample in accordance with the Ideal Gas Law. However, second order effects may include a slight thermal expansion of the White cell itself, thereby changing its pathlength. Further a redistribution of the population of the molecules towards higher rotational energy states because of the greater thermal energy available is likely to result. These effects will change the intensity and shape of the sample's spectrum in ways not accounted for by the Ideal Gas Law. Normally this effect is not very large. However, when trying to measure ratios such as $^{13}CO_2:^{12}CO_2$ in a set of samples with a precision 0.01%, such second order effects can be disastrous and must be either fully accounted for or avoided in the first instance. The best approach is avoidance through very tight control over the pressure and temperature stability of the instruments and the sample. Thus a set of samples is best analysed at the same temperature and pressure to within ±0.1 K and ±0.1 torr respectively. This is achieved in the preferred embodiment by precise, automated thermostatting and temperature and pressure control and the use of the outer box 37 as a thermal isolator.

Computer Processing of Results

Unfortunately, the spectrum acquired as a result of analysis of a sample can be subject to a number of fluctuations which must be accounted for. It is therefore necessary to undertake a process of calibration of the spectrometer/detector arrangement and the quantitative analysis of the spectra it produces.

It is desired to introduce air and gas samples of unknown makeup into the White cell 22, collect an FTIR spectrum of the unknown sample, and, by analysing that spectrum, determine the concentrations of several of the constituent gases in the sample. To do this it is necessary to determine a set of rules to quantitatively relate features in the spectrum of a mixture of species directly to the mixing ratios of individual species in the mixture and to determine how to extract the mixing ratio information. The traditional way of doing this is to introduce several samples of known makeup to the instrument and obtain their spectra. It is then possible to quantify the correlations between an individual species' mixing ratio and the intensity of certain features in the absorbance spectrum of a mixture containing that species. If enough different mixtures of precisely known constitution are analysed the instrument can be calibrated. The spectrum of an unknown sample can then be analysed in the light of what has been learnt from the behaviour of the spectra of the known samples.

In practice this is not easy to achieve. It is difficult, time consuming and expensive to construct a suitably large set of calibration samples from mixtures of real gases. It is similarly time consuming to measure the spectra of all these calibration samples. Furthermore, if the integrity of the instrument's calibration is to be monitored and maintained, calibration would need to be a regular practice since instrument response may drift in time. Also, if one of the measurement parameters, (e.g. sample pressure in the White cell), was changed the instrument would need full recalibration under the revised conditions. In real practice, the instrument would rarely, if ever, be properly calibrated, diminishing the quality of data retrieved from its spectra.

In accordance with the present invention, the arrangement 20 is calibrated against a series of synthetic spectra in accordance with the following theoretical analysis.

Theory

The calculation of synthetic spectra is based on a compilation of absorption line parameters, which includes, for each absorption line of each molecule, the line frequency $v_o$, integrated line strength S, lower state energy level $E_o$ and pressure and temperature dependent Lorenzian half-width $\alpha_L$. One suitable line parameter set is the commonly used HITRAN, [L. S. Rothman et al, Journal of Quant. Spectrosc. Radiation Transfer, 48, 469 (1992)] which includes line parameters for 31 individual common atmospheric gases and in many cases, their isotopomers. Other known lists and pseudo-line parameters for heavy gases such as Freon-12 ($CF_2Cl_2$) could also be used.

Each absorption line of each molecule will contribute to the total optical depth of a sample at each wavenumber. For each absorption line k of molecule i the contribution to the monochromatic optical depth τ at wavenumber v is given by $$\tau_i^k(v) = \sigma_i^k(v) \cdot a_i \tag{1}$$

where $\sigma_i^k(v)$ is the absorption coefficient or cross-section at v and $a_i$ is the amount of component i, equal to the pathlength times the concentration. In common practice $\sigma_i^k(v)$ has units of $cm^2$ $molec^{-1}$ and $a_i$ has units of $molec.cm^{-2}$. The absorption coefficient is calculated from the integrated line strength by convolution with the true lineshape:

There are two main broadening mechanisms contributing to the lineshape. Doppler broadening is due to random molecular motion and leads to a Gaussian lineshape $$f_G(v) = \frac{1}{\alpha_G \sqrt{\pi}} \exp\left(-\frac{(v-v_o)^2}{\alpha_g^2}\right) \tag{2}$$

where $\alpha_G$ is the Gaussian half width at half height $$\alpha_G = \frac{v_o}{c} \sqrt{\frac{2kT}{m}} \tag{3}$$

where m is the molecular mass, K is Boltzmann's constant, T is absolute temperature and c is the speed of light.

Pressure broadening is due to collisions perturbing the molecular energy levels and leads to a Lorentzian lineshape contribution $$f_L(v) = \frac{\frac{\alpha_L}{\pi}}{(v-v_o)^2 + \alpha_L^2} \tag{4}$$

where $\alpha_L$ is the Lorenzian half-width at half-height and is proportional to the total pressure. The Lorentzian half-width at 1 atm and its temperature dependence are tabulated for each absorption line in the HITRAN database. The Gaussian half-width is calculated from the temperature and molecular weight. Typical values are around 0.7 $cm^{-1}$ $atm^{-1}$ for $\alpha_L$ and 0.003 $cm^{-1}$ for $\alpha_G$ for medium sized molecules at room temperature. Thus the Lorentz contribution dominates except at low pressures. The convolved lineshape is known as the Voigt profile.

The absorption coefficient $\alpha_i^k(v)$ is the convolution of the integrated line strength and the two lineshape contributions:

$$\alpha_i^k(v) = S_i^k \otimes [f_L(v)]_i^k \otimes [f_G(v)]_i^k \tag{5}$$

where $\otimes$ represents convolution. The integrated linestrengths are tabulated in the HITRAN database at 296K and must be corrected to the temperature of the calculation. The temperature correction due to the temperature dependence of the population of the lower state energy level and the (small) contribution from spontaneous emission is given by $$S(T) = S(296) \times \frac{Q(296)}{Q(T)} \times \frac{\exp\left(\frac{-c_2 E_o}{T}\right)}{\exp\left(\frac{-c_2 E_o}{296}\right)} \times \frac{\left(1 - \exp\frac{-c_2 v_o}{T}\right)}{\left(1 - \exp\frac{-c_2 v_o}{296}\right)} \tag{6}$$

where the Q's are the partition functions and $c_2$ is the second radiation constant (=hc/k=1.439 cm K).

The total monochromatic optical depth at frequency v for a single homogeneous layer is then the sum of the $\tau_i^k(v)$ over all absorption lines of all molecules:

$$\tau(v) = \sum_i \sum_k \tau_i^k(v) \qquad (7)$$

The transmission spectrum of the sample without instrumental effects is then given by $$T(v) = \frac{I(v)}{I_o(v)} = \exp[-\tau(v)] \qquad (8)$$

where $l_o(v)$ and $l(v)$ are the intensities before and after traversal of the absorbing sample within reasonable time limits. The corresponding absorbance spectrum, $A(v)$ os simply equal to $\tau(v)$.

However any spectrometer convolves the true intensity $l=l_o\exp[-\tau(v)]$ with an instrument lineshape function to produce the observed or measured spectrum. If the width of the instrument lineshape function is much narrower than the true monochromatic lineshape then the above relations for T and A will be good approximations, but this is often not the case. The instrument lineshape for a perfectly aligned spectrometer without phase errors is itself a convolution of an apodization lineshape, which depends on a weighting (apodization) applied to the interferogram as a function of optical path difference, and a rectangular lineshape whose width depends on the divergence of the collimated beam in the interferometer due to the finite input aperture. The width of the rectangular divergence or field-of-view (FOV) contribution is equal to $v\alpha^2/2$ where $\alpha$ is the divergence half angle, and $\alpha=\emptyset/2f$ where $\emptyset$ is the entrance aperture (collimator field stop) diameter in the spectrometer and f the focal length of the collimator. The maximum acceptable divergence angle is determined by the resolution and the maximum frequency in the spectrum. For an optimally chosen aperture $v_{max}\alpha^2=1/L$, where L is the maximum optical path difference in the interferometer, so that $$\phi = 2f\sqrt{\frac{1}{v_{max}L}} \qquad (9)$$

The consequent FOV rectangular contribution to the lineshape, 0.5/L, is somewhat narrower than the width of the narrowest apodizing function (boxcar, 0.603/L).

If $f_I(v)$ represents the instrument lineshape, the measured spectrum is then given by $$l'(v) = l(v) \otimes f_I(v) \qquad (10)$$

and the measured absorbance spectrum is $$A'(v) = -\log\left(\frac{I(v)\otimes f_I(v)}{I_o(v)\otimes f_I(v)}\right) \qquad (11)$$

Spectra l' or A' calculated as above should be identical to those obtained by an ideal FTIR spectrometer. In practice, as will be seen below, this is usually achievable in that good fits of measured spectra using calculated spectra can be obtained such that the residual spectrum after fitting (=fitted spectrum−real spectrum) is close to the real spectrum noise level. Any non-ideality in the FTIR spectrometer performance will appear in the residuals and provides valuable information on the possible errors in spectrometer performance.

The HITRAN line parameters are temperature-corrected in accordance with equation (6). The vibrational contributions to the partition functions are evaluated in the harmonic approximation and the rotational contributions are proportional to T for linear molecules and $T^{1.5}$ for non-linear molecules. The exponent for the temperature dependence of Lorentzian half-widths is taken from the HITRAN line parameters. The line positions and intensities form a "stick" spectrum of $\delta$ functions which is convolved with the aforementioned Lorentzian and Gaussian lineshape functions to obtain the monochromatic optical depth, $\tau_i(v)$. The algorithms for the convolution are described below. The single component optical depth spectrum for each gas is stored for later re-use. The optical depth is then summed over all absorbing molecules and the monochromatic transmission calculated as:

$$T(v) = \exp(-\tau(v))$$

Finally the monochromatic transmission spectrum is convolved with the instrument lineshape function (apodization and FOV) and converted to required y-axis units (transmittance or absorbance). This step matches the monochromatic spectrum to the instrumentally-degraded spectrum, including matching the point spacing to that of the real spectrum. Preferably, the final spectrum is saved for analysis by commercially available software packages such as LabCalc or Grams.

For a set of calibration spectra, the number of spectra required and the range of concentrations for each absorber are input and a set of spectra with random concentrations within the given ranges are calculated. A variable baseline can be optionally included in the set by treating the baseline offset, slope and curvature as additional pseudo-components, which allows the fitting of nor-zero baselines in real spectra. Similarly, if desired, one or two etalon spectra (i.e. channel spectra) can be included as extra pseudo-components in the calculation as simple cosine functions with fixed period and phase but variable amplitude to be fitted. The period and phase must be determined by inspection, for example, from the residuals after fitting without the channel spectra included. A simple cosine function is only an approximation to real channel spectra but inclusion can improve the fit markedly. Finally, the calibration-set calculation also preferably produces a list file of all calibration spectra and their species concentrations in a format suitable for with the aforementioned software packages.

For each molecule, the line parameters are convolved with the true Voigt lineshape line-by-line using the algorithm of Drayson [S. R. Drayson, Journal of Quant. Spectrosc. Radiat. Transfer 16, 611 (1976)]. The convolution with the instrument function is performed by means of Fourier transforms, taking advantage of the Fourier Convolution theorem. The monochromatic transmission spectrum is Fourier transformed, normalised, and multiplied by the selected apodizing function and the Fourier transform of the rectangular lineshape due to the finite FOV, being $\sin(\pi v \alpha^2 x/2)/(\pi v \alpha^2 x/2)$ is applied. The transformed spectrum is then truncated so that on back-transformation, the point spacing matches that of the real spectrum to which it is to be compared. The apodization function can be chosen from a number of commonly used functions such as boxcar, triangular, Happ-Genzel, or Norton-Beer functions.

In operational terms, one full run of the synthetic spectrum calculating program, henceforth known as MALT, is substantially equivalent to the generation of a full set of calibration spectra. Typically 40 spectra or 5 times the number of components, whichever is greater should be calculated. The number of calibration spectra required depends in part on deviations from the ideal Beer-Lambert Law; in an ideal Beer-Lambert case, if there are N components and no noise only N spectra are required. However as the spectra are generated synthetically on a computer within reasonable time limits, the cost in time of generating large calibration sets is negligible.

All spectral display, plotting and analysis can be carried out utilising commercially available software such as LabCalc or Grams (available from Galactic Industries Corp., New Hampshire, USA) using standard routines or customised programs. The Classic Least Squares software utilised was based on the Quant Classic package from Galactic Industries available as an add-on to LabCalc but customised for ease of use. The theory behind the CLS method is described by D M Haaland, R G Easterling and D A Vopika in Applied Spectroscopy, Volume 39, 73 (1985).

CLS (Classic Least Squares) analysis is one of several chemometric techniques developed in the last decade or so and ideally suited to the retrieval of quantitative information from spectra. Other suitable techniques include PLS (partial least squares) and PCR (principal component regression). There are a number of commercial software packages which incorporate one or several of these approaches.

CLS is a whole spectrum technique. Prior to the development of these chemometric techniques, analysis for a particular species in a spectrum would focus on a single absorbance peak known to be associated with that species. Using a set of calibration spectra, a relationship would have been derived between the height of the peak (or sometimes the area under it), and the amount of the species present in the sample. Measuring the height (or area) of the peak in the unknown spectrum would thus provide a direct measure of the unknown's concentration. CLS differs from this approach in that it enables the simultaneous analysis of many absorbance features across one or several regions of the spectrum. Hence, many spectroscopic peaks rather than just one are exploited. This is a far more efficient use of the information in the spectrum. Also the technique allows much more robust analysis of molecules that may have overlapping features in the spectrum. The result is the possibility of very precise measurements of several species simultaneously in the one sample, e.g. the trace gases CO, $N_2O$, $CH_4$, $CO_2$ in air.

CLS analysis has two steps, calibration and prediction. The first step has as its input the set of calibration spectra, such as may be generated using the MALT program and the HITRAN database as aforementioned. These are spectra of the known mixtures of gases, where the concentrations of the constituent species vary from spectrum to spectrum. From this set, the CLS calibration step extracts single-component spectra, i.e. the individual spectrum of each of the pure components, as it were not in a mixture. Thus, the output from the calibration step is another set of spectra, this time not of mixtures of components, but of single units of concentration of pure components.

The prediction step is, in a sense, the reverse of the calibration step. The input to the prediction step is a real spectrum of a mixture, the concentration of the individual components being unknown. The CLS analysis constructs a fitted spectrum to the real spectrum by adding together suitable amounts of the single-component spectra which have been previously derived in the calibration step, so that the difference between the fitted and the real spectrum is minimised. The amounts of each single component spectrum used to construct the fitted spectrum are then utilised as the concentrations of the components in the unknown sample.

Figure 3:
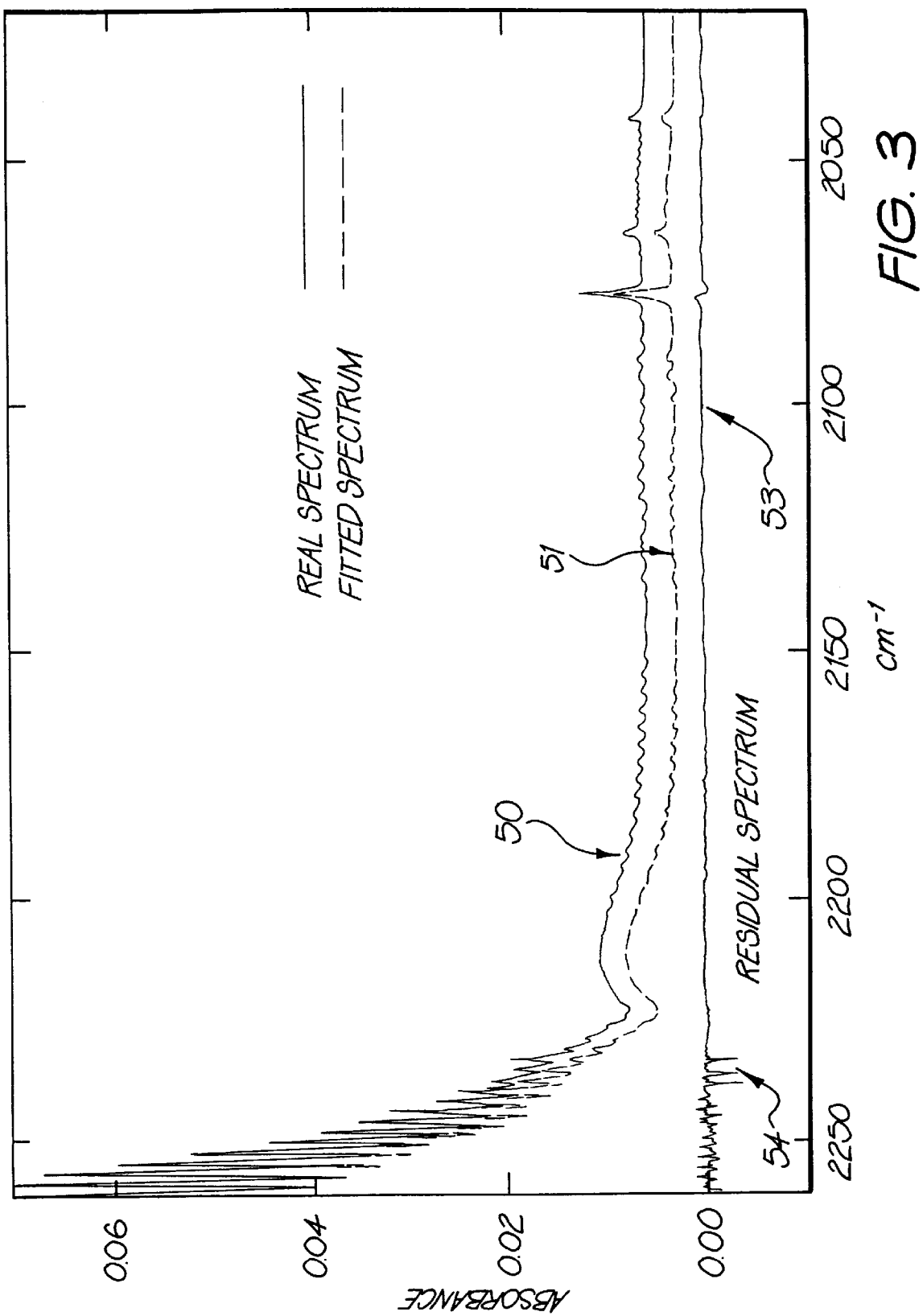
FIG. 3 illustrates the process of fitting a spectrum.

Referring now to FIG. 3, there is illustrated an example of the classic least squares best fit to a real spectrum. The real spectrum 50 is that associated with a clean air sample and the corresponding classic least squares fit 51 has been offset on the Y axis for clarity. Also shown is the residual spectrum 53 which is the difference between the real and fitted spectra. The residual spectrum 53 is useful as a diagnostic indicator of the quality of the fit. For example, in FIG. 3, there is a number of features 54 in the residual around 2240 $cm^{-1}$ indicating the presence of some unknown pollutant in the sample which may perturb the retrieved mixing ratios.

The aforementioned process utilising the calculated spectra derived from the HITRAN database and CLS analysis is utilised to carry out a first order, or primary, calibration of the instrument. The calibration reference standard in this case may be considered as the HITRAN database. A subsequent, more absolute calibration can be carried out by analysing real samples from a suite of calibration tanks containing air which had been well characterised by independent techniques. In the present embodiment the concentrations of the trace gases in these tanks were referenced to the best available international calibration scale, (maintained by NOAA/CMDL, US Dept of Commerce). It was found that there can be a systematic difference of up to 5% between the FTIR MALT/HITRAN calibrated concentrations and the concentrations on the international scale. This is thought due to limitations in some of the assumptions needed to be made in using MALT and HITRAN to calibrate the instrument. For many applications, systematic errors of less than 5% will not be a serious problem. However, for use of the preferred embodiment for some applications, e.g. monitoring of trace gas concentrations at clean air monitoring stations, or measurement of isotope ratios, a further level of calibration is often likely necessary. In these instances, the subsequent, more absolute calibration is achieved by sampling from a real calibration tank containing air whose concentrations have been measured on the international scale. This serves to relate the FTIR MALT/HITRAN calibration scale to the internationally accepted scale. It was found that usually, a simple linear equation is sufficient to transform the FTIR retrieved concentrations into concentrations on the international scale. For example, when the arrangement of FIG. 2 was utilised to analyse samples of air from the ambient atmosphere at half-hourly intervals continuously for several weeks, a sample of well characterised calibration gas was analysed under the same conditions every six hours. This enabled not only precise trace gas concentration retrievals, but also a level of accuracy believed to be of the order of 0.1%.

In utilising the CLS fitting procedure, it is necessary to fit the synthetically derived single component spectra to a real experimental spectrum of a mixture and hence a decision must be made as to which areas of the spectrum to utilise to do such a fitting. For example, referring to FIG. 4, there is illustrated a spectrum sample of air which includes 310 ppbv $N_2O$. The calculated spectrum for $N_2O$ is also illustrated 61, offset in the Y axis for clarity. It can be observed from FIG. 4, that virtually all the infrared absorbance of features for the species $N_2O$ occur in the region 2170–2270 $cm^{-1}$. In other words, the information provided by the spectrum about $N_2O$ is concentrated in that region. Intuition would suggestion that, in attempting to retrieve quantitative information about $N_2O$ from the spectrum, the optimal CLS calibration window will lie somewhere in the region 2170–2260 $cm^{-1}$.

However, there are significant gains to be made in precision by systematically rather than intuitively determining the ideal left and right edges of the calibration window for each individual species. Note that for $N_2O$ in air, half of the $N_2O$ band (2170–2225 $cm^{-1}$) 64 lies relatively clear of other absorbance bands with just a few weak CO lines overlapping with it. The other half (2225–2270 cm⁻) 65 lies under considerably stronger absorbance lines due mainly to $^{13}CO_2$. If a decision is made to fit $N_2O$ only in the region not obscured by $^{13}CO_2$, then this may throw away as much as half of the $N_2O$ information which could potentially have made the measurement more precise. If, on the other hand, all of the $N_2O$ information under $^{13}CO_2$ is included, the risk of having the $N_2O$ measurement perturbed by interference from the much stronger $^{13}CO_2$ absorbance features is much higher. The $N_2O$ information content may be diluted by the strong $^{13}Co_2$ information.

The ideal CLS calibration window for a species can be systematically determined solely by use of MALT calculated spectra and the CLS calibration procedure. The first step is to generate a set of spectra using MALT which closely simulates the line shape and range of concentrations of the instrumentally obtained spectra to be analysed. The wavenumber region of the MALT spectra should extend beyond the range of wavenumber regions to be considered for the optimal calibration window. First, a guess at the best left and right edges of the calibration window is made. Using these, along with the MALT calculated spectra as input, the CLS calibration step is undertaken. As well as producing a calibration, the CLS algorithm produces a statistical estimate of the precision of that calibration, (the Standard Error of Prediction; alternatively the similar statistical Root Mean Squared Deviation of the calibration curve can be used). That is, for a given set of input spectra and a given calibration window specified by its left and right edges, the CLS calibration step estimates how precisely it can retrieve each species' concentration from the spectroscopic information provided in that window. To systematically determine the optimal window for a given species, the CLS calibration step is performed many times, but each time with a different choice of calibration window. Then plot on a three-dimensional (x,y,z) plot of the Standard Error of Prediction versus left and right window edges is constructed. This will generate a three-dimensional "precision surface", the minimum point on which specifies the calibration window which will produce more precise retrievals of that species concentration from real spectra.

Figure 4:
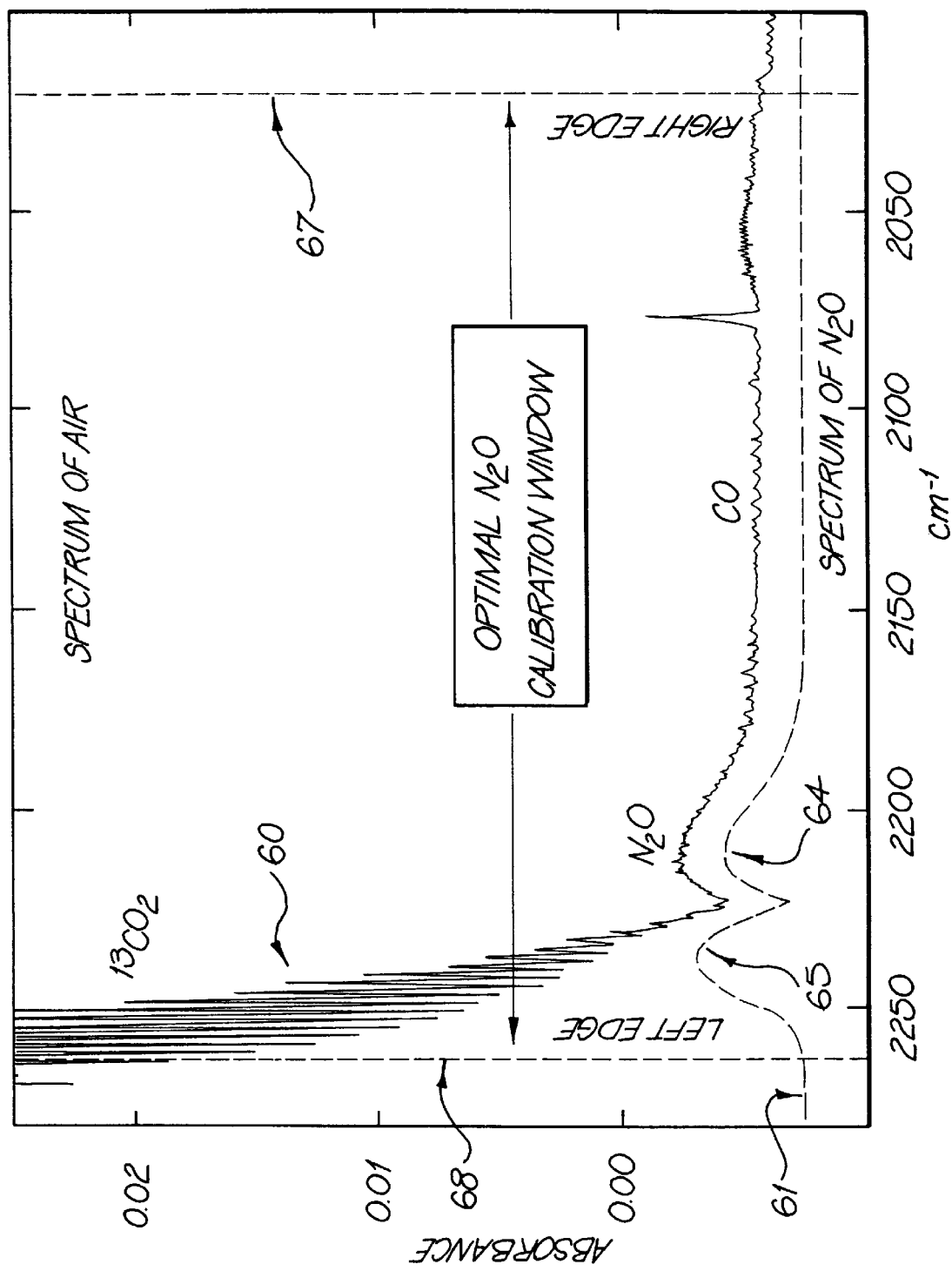
FIG. 4 illustrates the process of determining a calibration window.
Figure 5:
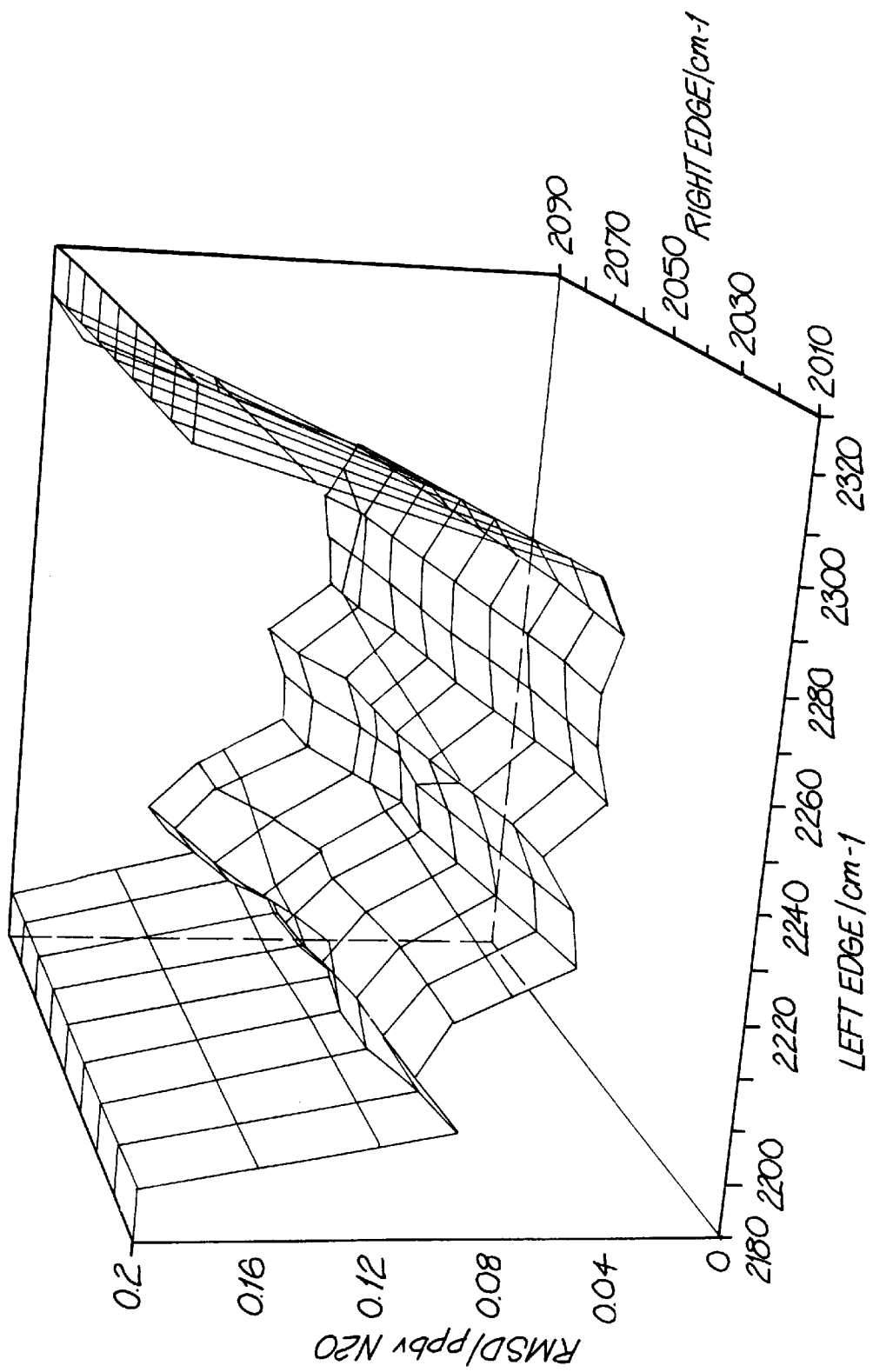
FIG. 5 illustrates an "error surface" for the position of a calibration window.
Figure 2:
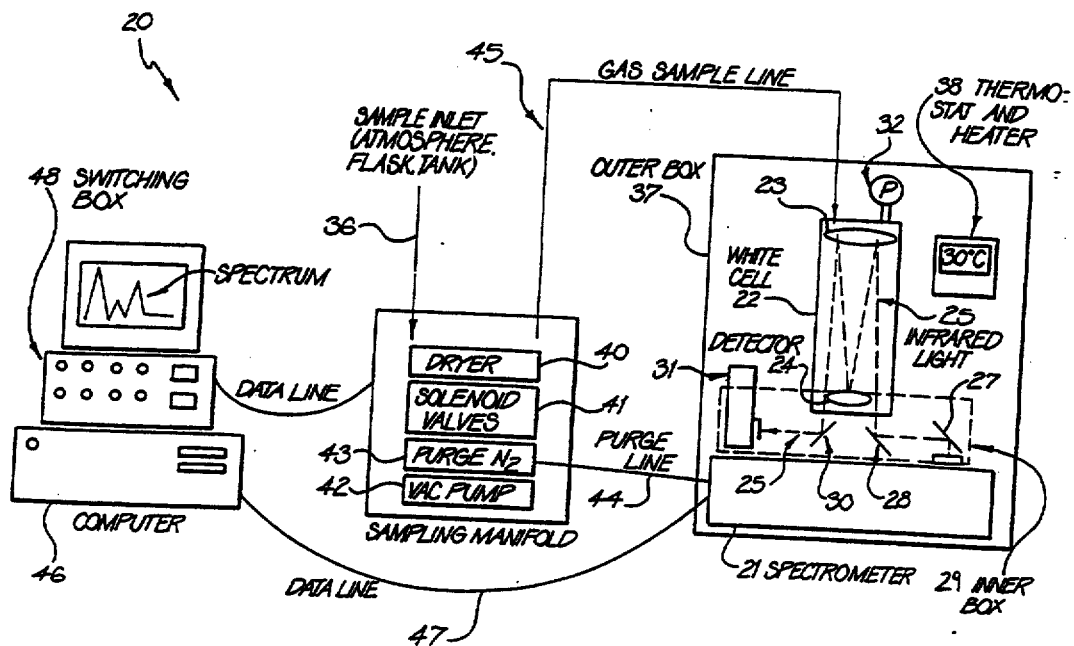

FIG. 5 illustrates such a precision surface for calibration of $N_2O$ measurements in the region of the spectrum bounded by 2010 cm⁻¹ and 2180 cm⁻¹. The position of the minima on this surface suggests that a prudent choice for an $N_2O$ calibration window would be the region 2020–2260 cm⁻¹. This optimal window is illustrated in FIG. 4 having right edge 67 and left edge 68. Choosing a left edge much lower than 2260 cm–1 results in a loss of measurement precision, due to failing to use all of the useful $N_2O$ information in the spectrum. On the other hand, choosing a left window edge much higher than 2260 cm⁻¹ leads to a loss of measurement precision due to the inclusion in the window of too much strong $^{13}CO_2$ information which somehow obscures or dilutes the $N_2O$ information content. Somewhat counterintuitively, the optimal right edge 67 for the $N_2O$ window is 2020 cm⁻¹, resulting in the inclusion of a large region where there is very little absorbance, by $N_2O$ or any other species. It is believed that the inclusion of such baseline regions into calibration windows is precisely because these regions serve to characterise the baseline. Only when the baseline is well characterised are the non-baseline absorbance features well constrained by reference to it, thus leading to improved measurement precision.

It is envisaged that other, more complex numerical optimization techniques such as simulated annealing, known to those skilled in numerical analysis may also lead to even further improvement in calibration window choice.

Further it is envisaged that, in use, the spectral windows can be precalculated for each species of interest. For example, one window can be determined for CO, one for $N_2O$ etc. Having precalculated each window, the relevant window border parameters can be pre-stored and loaded in as required.

Using the hardware, software and methods described in the previous sections, it has been found to be possible to measure the concentrations of the atmospheric trace gases $CO_2$, $CH_4$, $N_2O$ and CO with sensitivity and precision competitive with what was previously attainable only by employing gas chromatography and non-dispersive infrared analytical techniques. It is also believed that these FTIR measurements are linear over a range of concentrations which exceeds the range normally found in the atmosphere. In addition, the individual isotopic contributions $^{12}CO_2$ and $^{13}CO2$ to total $CO_2$ and hence the isotope ratio $^{12}CO_2$:$^{13}CO_2$ can be determined to a higher accuracy than previous FTIR techniques. The levels of measurement precision attainable in analysis of clean air by FTIR spectroscopy are summarised in the Table below where σ represents the standard deviation of a single measurement. The notation $\delta^{13}CO_2$ is a particular form of notation for expressing $^{13}C$:$^{12}C$ in $CO_2$ with respect to the standard reference scale. A precision (±σ) of 0.15 per mil in $\delta^{13}CO_2$ is equivalent to a $^{13}CO_2$:$^{12}CO_2$ ratio being measured to a precision of ±0.015%.

| Species | Clean Air Level | FTIR Precision ± σ | % |
|---|---|---|---|
| CO | 50 ppbv | 0.4 | 0.8% |
| $N_2O$ | 311 ppbv | 0.3 | 0.09% |
| $CH_4$ | 1680 ppbv | 1.2 | 0.07% |
| $CO_2$ | 358 ppmv | 0.1 | 0.03% |
| $\delta^{13}CO_2$ | −7.9 permil | 0.15 | — |

The arrangement of the preferred embodiment can be utilised to conduct isotopic analysis of samples. In particular, the preferred embodiment can be utilised to study the isotopic analysis of breath samples for the purposes of studying facets of human metabolism and certain disorders and infections.

Diagnosis of breath analysis is becoming increasingly popular. The breath tests often provide direct information unattainable by other means. Alternatively, they may provide information which is attainable only by far more invasive, expensive and dangerous means. An example is the use of the $^{13}C$-urea breath test for the diagnosis of infection by the stomach-ulcer causing bacterium *Helicobacter pylori*. The traditional means of diagnosis is by the invasive procedure of gastroscopy and biopsy of the stomach lining. The use of breath testing to diagnose H. pylori infection is growing, but is hindered by the expense of the Isotope Ratio Mass Spectrometry instrumentation necessary in the current main commercially available technique for analysing the breath samples. The preferred embodiment utilising FTIR spectroscopy offers a less expensive alternative. Tests on infected subjects' breath samples have already shown that the preferred embodiment has the necessary sensitivity and precision to perform this analysis.

There are a number of different known $^{13}C$-based breath tests for various conditions and disorders. They all rely on the same principle. In each case a small amount of a substrate is labelled with a $^{13}C$ atom, where normally there would have been a $^{12}C$ atom. $^{13}C$ is not radioactive ($^{14}C$ is)

and is perfectly safe to ingest. The substrate is usually a sugar, a fat or some other simple molecule such as urea metabolised in the body. When the labelled substrate is ingested and metabolised, one of the metabolic products is $^{13}CO_2$. This rapidly passes into the bloodstream and then into the lungs from where it is exhaled in the breath. The rate at which the $^{13}CO_2$ appears in the breath after ingestion of the $^{13}C$ labelled substrate provides information about the processes that the labelled substrate has undergone. For example, in the $^{13}C$-urea breath test, only those subjects infected with Helicobacter pylori will have large enrichments of $^{13}CO_2$ in their breath in the half hour following ingestion of the substrate. This is because it is the bacterium itself which breaks $^{13}C$-urea down into $^{13}CO_2$ and ammonia. Referring now to FIG. 6, there is illustrated a plot of $^{13}CO_2$ ratio over a 30 minute period for a patient having small quantities of $^{13}C$ labelled urea over a 30 minute period from ingestion. A first plot 70 illustrates the $^{13}CO_2:^{12}CO_2$ ratio for an infected patient and the second plot 71 illustrates the ratio for a non-infected patient.

The level of enrichment of $^{13}CO_2$ in the breath is however, very small in all of the aforementioned tests. Typically a positive test result will be indicated by a change of only 0.5% to 2% in the $^{13}CO_2: ^{12}CO_2$ ratio in the breath. However, the preferred embodiment is sufficiently sensitive to measure this level of change.

The preferred embodiment is also suitable for use with other $^{13}C$ breath tests including but not limited to:

1. A $^{13}C$-lactose breath test utilised in the diagnosis of carbohydrate malabsorption. Lactose malabsorption is a well known cause of diarrhoea and abdominal complaints. Other sugars, fructose sucrose, glucose can be tests for malabsorption also.

2. A $^{13}C$-triolein breath test is utilised in the diagnosis and monitoring of fat malabsorption usually due to disease or the pancreas, particularly in patients with cystic fibrosis.

3. A $^{13}C$-glycoholic acid breath test is utilised in the assessment of bile acid metabolism, with implications for cancer of the large bowel. This test is also used to diagnose bacterial overgrowth in the small intestine.

4. A $^{13}C$-aminopyrine breath test is used in the diagnosis of liver function, e.g. cirrhosis of the liver.

Further, other gas phase molecules with significant absorbance features in the infrared region are amenable to quantitative analysis by FTIR using the techniques described above.

Molecular species amenable to quantitative concentration analysis include;

Carbon dioxide ($CO_2$)
Methane ($CH_4$)
Carbon monoxide (CO)
Nitrous oxide ($N_2O$) as already mentioned; and also
Water ($H_2O$)
Ammonia ($NH_3$)
Sulfur dioxide ($SO_2$)
Hydrogen sulfide ($H_2S$)
Ozone ($O_3$)
Acetylene ($C_2H_2$)
Ethane ($C_2H_6$)
Sulfur hexafluoride ($SF_6$)
Acetone ($CH_3COCH_3$)
Formaldehyde ($CH_2O$)

Isotopomeric species amenable to quantitave isotope ratio analysis include;

$^{16}O^{12}C^{16}O$, $^{16}O^{13}C^{16}$, $^{17}O^{12}C^{16}O$, $^{18}O^{13}C^{16}O$, $^{17}O^{13}C^{16}O$ (i.e. $CO_2$ isotopomers)

$^{12}CH_4$, $^{13}CH_4$, $^{12}CDH_3$ (i.e. $CH_4$ isotopomers)

$^{12}C^{16}O$, $^{13}C^{16}O$, $^{12}C^{18}O$, $^{12}C^{17}O$ (i.e. CO isotopomers)

$^{14}N^{14}N^{16}O$, $^{15}N^{14}N^{16}O$, $^{14}N^{14}N^{18}O$ (i.e. $N_2O$ isotopomers)

$H_2^{16}O$, $HD^{16}O$, $H_2^{18}O$, $H_2^{17}O$ (i.e. $H_2O$ isotopomers)

This list is not exhaustive.

Some of these analyses can be performed on unprocessed air, breath or other gas phase mixtures. Others require the unprocessed sample to undergo a process of extraction and/or concentration of the species of interest prior to FTIR analysis.

Further the aforementioned techniques can be extended to concentration and isotope ratio analysis of species which are not in the gas phase. This would involve a preanalysis chemical process whereby the analyte was quantitatively converted to one of the species which is in the gas phase. For example, the relative abundance of $^{12}C$ and $^{13}C$ in a piece of wood could be determined by first combusting the wood. Analysis of other organic and geological samples is achieved simultaneously.

It would be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

We claim:

1. A method of performing a primary calibration of a spectrometer device comprising the steps of:

calculating a theoretical spectral response function for a series of candidate chemical substances;

convolving said theoretical spectral response function with a spectrometer instrument response function corresponding to said spectrometer device so as to produce an expected response function for said series of candidate chemical substances; and utilising said expected response function as the calibration of said spectrometer device in the subsequent measurement of chemical substances.

2. A method as claimed in claim 1 further comprising the step of:

measuring a series of calibrated standard chemical substances to determine a subsequent calibration of said spectrometer device and said utilising step further comprises utilising said subsequent calibration and said primary calibration as the calibration of said spectrometer device.

3. A method as claimed in claim 1 wherein said theoretical response function includes a correction factor associated with Doppler broadening of said spectral response.

4. A method as claimed in claim 1 wherein said theoretical response function includes a correction factor associated with pressure broadening of said spectral response.

5. A method as claimed in claim 1 wherein said theoretical response function includes a correction factor associated with temperature correction of said spectral response.

6. A method as claimed in claim 1 wherein said spectrometer instrument response function includes a correction factor associated with field of view.

7. A method as claimed in claim 1 wherein said spectrometer instrument response function includes a correction factor associated with spectral resolution.

8. A method as claimed in claim 1 wherein said spectrometer instrument response function includes a correction factor associated with wave number shift.

9. (A method as claimed in claim 1 wherein said spectrometer instrument response function includes a correction factor associated with spectral noise.

10. A method as claimed in claim 1 wherein said spectrometer instrument response function includes a correction factor associated with apodization.

11. A method of determining a spectral window within which to fit a synthetically calculated spectral trace to an experimentally acquired spectral trace, said method comprising the steps of:

choosing a series of candidate windows determining a likely error measure associated with the fitting of said experimental spectral trace for each of said series of candidate windows;

utilising said likely error measure associated with each of said fittings to determine a final window having substantially the lowest likely error measure; and utilising said final window as said spectral window.

12. A method as claimed in claim 11 wherein said fitting is a classic least squares decomposition of said spectral trace.

13. A method as claimed in claim 11 wherein said fitting is a classic partial least squares fit of said spectral trace.

14. A method as claimed in claim 11 wherein said series of candidate windows are derived from permutations of window edges which are at substantially equally spaced intervals within an overall total possible chosen spectral window.

15. A method of determining a trace gas concentration in a gas sample utilising Fourier Transform Infra-Red Spectroscopy, said method comprising the following steps (i) to (iii) of:

(i) synthetically calibrating a spectrometer by the steps of:
  (a) calculating a theoretical spectral response function for a series of candidate chemical substances;
  (b) convolving said theoretical spectral response function with a spectrometer instrument response function corresponding to said spectrometer device so as to produce an expected response function for said series of candidate chemical substances; and
  (c) utilising said expected response function as the calibration of said spectrometer device in the subsequent measurement of chemical substances;

(ii) determining a spectral window within which to fit a calculated spectral trace to an experimental spectral trace by the steps of;
  (a) choosing a series of candidate windows;
  (b) determining the likely error measure associated with a fitting of said spectral trace for each of said series of candidate window;
  (c) utlising said likely error measure associated with each of said fitting to determine a final window having substantially the lowest likely error measure; and
  (d) utilising said final window as said spectral window; and (iii) utilising said calibration and said spectral window to fit a calculated spectral trace to a spectral trace measured by the spectrometer and to thereby determine the concentrations of constituent gases.

16. A method as claimed in claim 15 wherein said spectrometer measures said gas sample in a controlled atmosphere wherein the temperature is controlled to within 0.1 degrees celcius.

17. A method as claimed in claim 15 wherein said trace gases is at least one gas selected from the group consisting of $CO_2$, $CH_4$, $CO$, $N_2O$, $H_2O$, $NH_3$, $SO_2$, $H_2S$, $O_3$, $C_2H_2$, $C_2H_6$, $SF_6$, $CH_3COCH_3$, $CH_2O$ and their isotopomers.

18. A method as claimed in claim 15 wherein said concentrations include those of $^{12}CO_2$ to $^{13}CO_2$, which are then utilised to determine the isotope ratio $\delta^{13}CO_2$.

19. A method as claimed in claim 18 wherein said traces gases are analysed from a sample of a patients's breath.

20. A method as claimed in claim 19 wherein said ratio is utilised to determine if said patient has one of the disorders selected.

21. A spectrometer for measuring gas concentrations and isotope ratios in gases comprising;

a sample cell for containing a gas phase sample, a pressure monitor for measuring the pressure within said cell, a temperature monitor for measuring the temperature within said cell, an interferometer, a source of infrared radiation directing infrared radiation along a path through said interferometer and said cell, a detector for measuring and recording the intensity of infrared radiation leaving said cell along said path, an inner enclosure enclosing said path from said source to said sample cell and from said sample cell to said detector, said inner enclosure having a connection to a source of infrared transparent gas, an outer enclosure enclosing said inner enclosure and including a constant temperature control device to maintain a constant temperature within the outer enclosure, control device for controlling the introduction of gas samples to the sample and a data processor for generating synthetic calibration spectra and for fitting the synthetic calibration spectra to a measured spectra.

22. The spectrometer according to claim 21, wherein said source of infrared radiation, interferometer, sample cell and detector are enclosed within said outer enclosure.

23. The spectrometer according to claim 21, wherein the constant temperature control device comprises a temperature sensor, thermostat, heating device and fan to maintain a constant temperature by circulating heated air within said outer enclosure.

* * * * *

UNITED STATES PATENT AND TRADEMARK OFFICE
CERTIFICATE OF CORRECTION

PATENT NO. : 5,838,008
DATED : November 17, 1998
INVENTOR(S) : Esler et al

It is certified that error appears in the above-identified patent and that said Letters Patent is hereby corrected as shown below:

In the Drawing Sheet, Fig. 2 , sheet 4 of 8 should be deleted and be replaced with Fig. 2 , sheet 4 of 8, as shown on the attached page.

UNITED STATES PATENT AND TRADEMARK OFFICE
CERTIFICATE OF CORRECTION

PATENT NO. : 5,838,008
DATED : November 17, 1998
INVENTOR(S) : Esler et al

It is certified that error appears in the above-identified patent and that said Letters Patent is hereby corrected as shown below:

On the title page: Item [56] Reference Cited:

OTHER PUBLICATIONS, in the reference authored by L. Tyson, et al., change "$^{12}C$" to --$^{13}C$--.

UNITED STATES PATENT AND TRADEMARK OFFICE
CERTIFICATE OF CORRECTION

PATENT NO. : 5,838,008
DATED : November 17, 1998
INVENTOR(S) : Esler et al.

It is certified that error appears in the above-identified patent and that said Letters Patent is hereby corrected as shown below:

In column 10, line 8, of the Letters Patent, "(v)" should read --(*v*)--.

In column 12, line 40, of the Letters Patent, after "Fig. 2" delete the paragraph break.

In column 13, line 12, of the Letters Patent, "Co₂" should read --$CO_2$--.

In column 13, line 36, of the Letters Patent, after "Then" delete "plot on".

In column 13, line 50, of the Letters Patent, "cm-1" should read as --$cm^{-1}$--.

In column 14, line 18, of the Letters Patent, "$^{13}CO2$" should read --$^{13}CO_2$--.

In column 14, line 54, of the Letters Patent, "H. pylori" should read --*H. pylori*--.

In column 15, lines 15, 16, 17 and 18, of the Letters Patent, "Referring now to FIG. 6, there is illustrated a plot of $^{13}CO_2$ ratio over a 30 minute period for a patient having small quantities of $^{13}C$ labelled urea over a 30 minute period from ingestion" should read --Referring now to FIG. 6 there is illustrated a plot of the $^{13}CO_2$ $^{12}CO_2$ ratio over the 30 minute period after two patients each ingested a small quantity of $^{13}C$-labelled urea-- .

In column 16, line 18, of the Letters Patent, "simultaneously" should read -- similarly-- .

In claim 9, column 16, line 65, after "9.", delete --(--.

UNITED STATES PATENT AND TRADEMARK OFFICE
CERTIFICATE OF CORRECTION

PATENT NO. : 5,838,008
DATED : November 17, 1998
INVENTOR(S) : Esler et al.

It is certified that error appears in the above-identified patent and that said Letters Patent is hereby corrected as shown below:

In column 3, line 45, of the Letters Patent, "the ratio of a $^{12}C$ to $^{13}C$" should read -- the ratio of $^{12}C$ to $^{13}C$ --.

In column 4, line 17, of the Letters Patent, "multi-path" should read --multi-pass--.

In column 4, line 27, of the Letters Patent, after the word "detector" delete the paragraph break.

In column 4, line 49, of the Letters Patent "box 40" should read --box 29--.

In column 4, line 52, of the Letters Patent "box 40" should read --box 29--.

In column 4, line 53, of the Letters Patent, "box 40" should read --box 29--.

In column 4, line 55, of the Letters Patent, "box 40" should read --box 29--.

In column 5, line 1, of the Letters Patent, "box 40" should read --box 29--.

In column 5, line 19, of the Letters Patent, "moans" should read -- means --.

In column 7, line 56, of the Letters Patent, "v" should read --$\nu$--.

In column 8, line 6, of the Letters Patent, "(v)" should read --($\nu$)--.

In column 8, line 7, of the Letters Patent, "v" should read --$\nu$--

UNITED STATES PATENT AND TRADEMARK OFFICE
CERTIFICATE OF CORRECTION

PATENT NO.  : 5,838,008
DATED       : November 17, 1998
INVENTOR(S) : Esler et al.

It is certified that error appears in the above-identified patent and that said Letters Patent is hereby corrected as shown below:

In column 8, line 9, of the Letters Patent, "(v)" should read --($v$)--.

In column 8, line 43, of the Letters Patent, "v" should read --($v$)--.

In column 9, line 1, of the Letters Patent, "v" should read --$v$--.

In column 9, line 2, of the Letters Patent, "(v)" should read --($v$)--.

In column 9, line 12, of the Letters Patent, "1o(v) and 1(v)" should read --L$_o$($v$) and I($v$)--.

In column 9, line 14, of the Letters Patent, "A(v)" should read --A($v$)--.

In column 9, line 14, of the Letters Patent, "os" should read --as--.

In column 9, line 15, of the Letters Patent, "(v)" should read --($v$)--.

In column 9, line 17, of the Letters Patent, "(v)" should read --($v$)--.

In column 9, line 30, of the Letters Patent, "to v" should read --to $v$--.

In column 9, line 36, of the Letters Patent, "v" should read --$v$--.

In column 9, line 45, of the Letters Patent, "(v)" should read --($v$)--.

In column 9, line 55, of the Letters Patent, "1" should read --I--.

UNITED STATES PATENT AND TRADEMARK OFFICE
CERTIFICATE OF CORRECTION

PATENT NO. : 5,878,008
DATED : November 17, 1998
INVENTOR(S) : Esler et al.

It is certified that error appears in the above-identified patent and that said Letters Patent is hereby corrected as shown below:

In Claim 13, line 21, after the word "a" delete the word "classic".

In claim 18, line 12, "to $^{13}CO_2$" should read --and $^{13}CO_2$-- .

In claim 19, line 15, "traces" should read --trace-- .

In claim 20, column 18, line 19, after "selected" insert --from the group consisting of a helicobacter pylori infection, fat malabsorption, sugar malabsorption, liver disfunction, and lactose malabsorption--.

Signed and Sealed this

Twenty-fifth Day of April, 2000

Attest:

Q. TODD DICKINSON

*Attesting Officer*       *Director of Patents and Trademarks*